Figure 1:
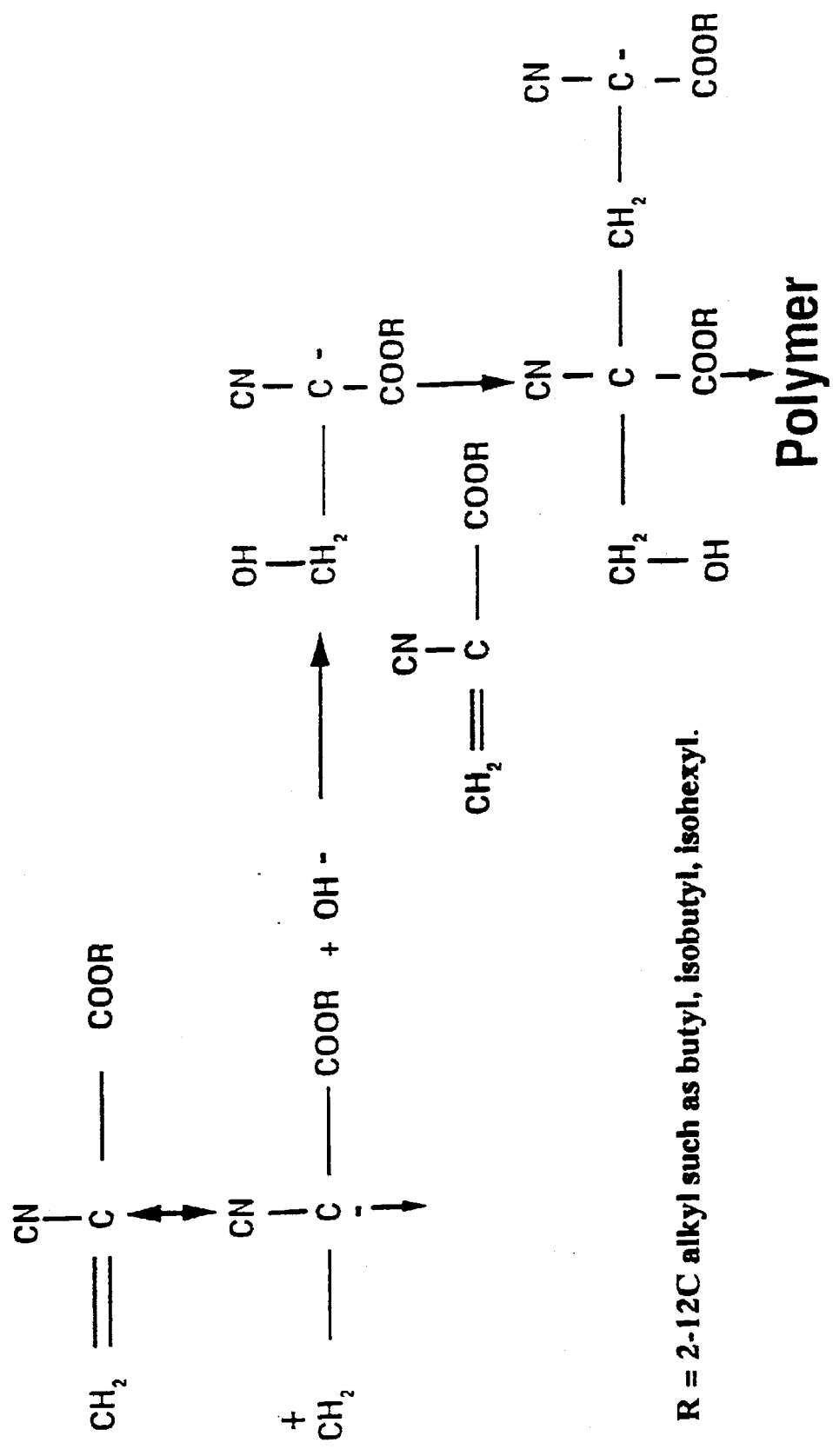

United States Patent [19]

Ramtoola

[11] Patent Number: 5,641,515
[45] Date of Patent: Jun. 24, 1997

[54] CONTROLLED RELEASE BIODEGRADABLE NANOPARTICLES CONTAINING INSULIN

[75] Inventor: Zeibun Ramtoola, Dublin, Ireland

[73] Assignee: Elan Corporation, plc, Athlone, Ireland

[21] Appl. No.: 474,161

[22] Filed: Jun. 7, 1995

[30] Foreign Application Priority Data

Apr. 4, 1995 [IE] Ireland ............................. 950237

[51] Int. Cl.$^6$ ........................................ A61K 9/14
[52] U.S. Cl. .............. 424/189; 424/490; 424/493; 427/212; 427/213.34; 427/213.36; 428/402; 428/402.2; 428/402.21; 428/402.24; 428/403
[58] Field of Search .................... 424/489, 490, 424/493; 427/212, 213.34, 213.36; 428/402, 402.2, 402.21, 402.24, 403

[56] References Cited

PUBLICATIONS

Al Khouri, N. et al., Development of a new process for the manufacture of polyisobutylcyanoacrylate nanocapsules, *Int. J. Pharm.*, 28:125–32 (1986).
Couvreur, P. et al., Polycyanoacrylate nanocapsules as potential lysosomotropic carriers: preparation, morphological and sorptive properties, *J. Pharm. Pharmacol.*, 31;331–2 (1979).
Guise, V., et al., Vidarabine–Loaded Nanoparticles: A Physicochemical Study, *Pharmaceutical Res.*, 7:736–41 (1990).
Douglas, S. et al., Particle Size and Size Distribution of Poly(butyl 2–cyanoacylate) Nanoparticles *J. Colloid Interface Science*, 103: 154–63 (1985).
Tasset, Ch., et al., Polyisobutylcyanoacrylate nanoparticles as sustained release system for calcitonin, *J. of Controlled Release*, 33:23–30 (1995).
Kattan, Joseph, et. al, Phase I Clinical Trial and Pharmacokinetic Evaluation of Doxorubicin Carried by Polyisohexylcyanoacrylate Nanoparticles, *Investigational New Drugs*, 10: 191–199 (1992).

Vansnick, L. et al, Molecular Weights of Free and Drug–Loaded Nanoparticles, *Pharmaceutical Research*, 36–41 (1985).
Guzman, M. et. al., Formation and Characterisation of Cyclosporin–Loaded Nanoparticles, *Pharm. Sciences*, 82, 498–502 (1993).
Douglas, et al., Particle size and size distribution of poly(butyl–2–cyanoacrylate) nanoparticles. I. Influence of physicochemical factors,, *J. Colloid and Interface Science*, 101: 149–58 (1984).
Douglas, et al., Poly(butyl 2–cyanoacrylate0 nanoparticles with differing surface charges, *J. of Controlled Release*, 3: 15–23 (1986).
Damge, C. et al., New approach for oral administration of insulin with polyalkylcyanoacrylate nanocapsules as drug carrier, *Diabetes*, 37:246(51) (1988).
Lowe, P. et al., Calcitonin and Insulin in Isobutylcyanoacrylate Nanocapsules: Protection Against Proteases and Effect on Intestinal Absorption in Rats, *J. Pharma. Pharmacol.*, 46;547–52 (1994).
Gautier, J. et al., Biodegradable nanoparticles for subcutaneous administration of growth hormone releasing factor (hGRF) *J. Controlled Release*, 20:67–77 (1992).

*Primary Examiner*—Terressa Mosley
*Attorney, Agent, or Firm*—Mary L. Severson

[57] ABSTRACT

A controlled release pharmaceutical formulation comprises nanoparticles formed of a biodegradable polycyanoacrylate polymer in which insulin is entrapped, the insulin being complexed to the polycyanoacrylate. These particles are capable of releasing bioactive insulin in vivo at a slower release rate than nanoparticles in which the insulin is free. The formulation may comprise a mixture of nanoparticles in which the insulin is free and nanoparticles in which it is complexed, so as to obtain the desired release profile. The nanoparticles have a preferred loading of 15–25% w/v insulin and a preferred size of 100–400 nm. Administration may be oral or parenteral, and for oral administration, an enteric coating may be provided to target release to the small intestine. Complexing of the insulin is achieved by the polymerisation of cyanoacrylate monomer in the presence of insulin at a low pH, preferably at about pH=2.

22 Claims, 3 Drawing Sheets

CONTROLLED RELEASE BIODEGRADABLE NANOPARTICLES CONTAINING INSULIN

I. FIELD OF THE INVENTION

This invention relates to controlled release biodegradable nanoparticle formulations and, in particular, biodegradable polyalkylcyanoacrylate nanoparticles containing insulin or insulin analogues.

II. BACKGROUND OF THE INVENTION

Polyalkylcyanoacrylate nanoparticles have been studied as potential drug carriers for sustained release formulations, for drug targeting and for improving the bioavailability of peptides and proteins such as insulin, calcitonin and growth hormone releasing factor (Damgé, C. et al., *Diabetes*, 37:246(51) (1988); Lowe, P. et al., *J. Pharma. Pharmacol.*, 46:547–52 (1994); and Gautier, J. et al., *J. Controlled Release*, 20:67–78 (1992)). The short chain cyanoacrylate monomers, such as n-butyl, isobutyl and isohexylcyanoacrylate, are typically used because of their short degradation times and low toxicities.

Two methods are commonly employed for the preparation of these nanoparticles: the interfacial polymerisation method and the anionic polymerisation method. In the interfacial polymerisation method, the monomer and the drug are dissolved in an organic phase with polymerisation occurring at the organic-aqueous interface upon addition of the organic phase to an aqueous phase (Al Khouri, N. et al., *Int. J. Pharm.*, 28:125–32 (1986). This method produces nanocapsules. In general, prior art peptide loaded nanoparticles have been produced by this technique (see, e.g., EP-A-0 608 207; EP-A-0 447 318; and FR-A-2,515,960).

Anionic polymerisation occurs in aqueous media at low pH and is catalyzed by hydroxyl ions. In this method, the drug can be incorporated within the nanoparticle, adsorbed onto the nanoparticles or a combination of both depending on the time of addition of the drug to the polymerisation medium (Couvreur, P. et al., *J. Pharma. Pharmacol.*, 31:331–2 (1979)).

Vidarabine-associated polyalkylcyanoacrylate nanoparticles, which result from vidarabine chemically interacting with the cyanoacrylic monomer during the polymerisation process, have been made using the anionic polymerisation method modified by the mandatory inclusion of dioctylsulfosuccinate in the aqueous media. However, formation of the polyalkylcyanoacrylate/vidarabine complex inactivated the biological activity of the vidarabine (Guise, V., et al., *Pharmaceutical Res.*, 7:736–41 (1990)).

Administration of exogenous insulin can ameliorate metabolic abnormalities in type II diabetes by compensating for reduced endogenous insulin secretion, reducing excessive hepatic glucose production and stimulating glucose uptake. Additionally, non-substitutional insulin administration in non-insulin dependent diabetes is indicated where, without it, satisfactory compensation of diabetes is not achieved. Side effects possible from insulin therapy include weight gain, hyperinsulinemia and hypoglycemia.

Although single or multiple daily subcutaneous injections of insulin are the mainstay of insulin delivery techniques, several other methods of insulin delivery are now available or in development, including (a) continuous subcutaneous insulin infusion by a wearable infusion pump; (b) total or segmental transplantation of a pancreas; (c) transplantation of isolated islet cells; (d) implantation of a programmable insulin pump; (e) oral, nasal, rectal and transdermal mechanisms of insulin delivery; (f) administration of insulin analogues; (g) implantation of polymeric capsules which give continuous or time-pulsed release of insulin; and (h) implantation of a biohybrid artificial pancreas which uses encapsulated islets. Despite these advances, the ideal delivery of insulin to patients has yet to be developed. For instance, subcutaneous and oral methods of insulin delivery do not currently mimic physiological insulin needs and transplantation requires risky immunosuppression.

Thus, there exists a need for improved insulin formulations, particularly controlled release bioactive oral formulations including those targeted to the small intestine and controlled release parenteral formulations to mimic physiological insulin needs.

III. SUMMARY OF THE INVENTION

This invention provides a controlled release pharmaceutical formulation, which comprises insulin entrapped in a biodegradable polyalkylcyanoacrylate polymer to form nanoparticles, wherein the insulin is complexed to the polyalkylcyanoacrylate. The biodegradable polyalkylcyanoacrylate polymer is suitably n-butylcyanoacrylate, isobutylcyanoacrylate or isohexylcyanoacrylate monomers or mixtures thereof.

Surprisingly, this invention discloses that at low pH and otherwise typical anionic polymerisation conditions, insulin complexes with polycyanoacrylate during the polymerisation step, forming polyalkylcyanoacrylate-complexed insulin-loaded nanoparticles. At higher pH, the insulin does not complex with the polymer but, rather, is incorporated into nanoparticles as free insulin. Further surprisingly, the polyalkylcyanoacrylate-complexed insulin-loaded nanoparticles are capable of releasing bioactive insulin in vivo. The rate of insulin release from these polyalkylcyanoacrylate-complexed insulin-loaded nanoparticles is slower than that from corresponding free insulin-loaded polyalkylcyanoacrylate nanoparticles. At an intermediate pH, the nanoparticles can be a natural mixture of free and complexed insulin.

Thus, this invention provides oral and parenteral formulations containing polyalkylcyanoacrylate-complexed insulin-loaded nanoparticles that are capable of releasing pharmaceutically effective amounts of bioactive insulin in a controlled fashion to satisfy physiological insulin needs when orally or parenterally administered to a subject, particularly a human. Further, the controlled release nature of these formulations makes possible the targeting of insulin to the small intestine when administered orally, which enhances the bioavailability of the insulin. Optionally, these oral and parenteral formulations may comprise a mixture of polyalkylcyanoacrylate-complexed insulin-loaded nanoparticles and free insulin-loaded polyalkylcyanoacrylate nanoparticles.

The biodegradable nanoparticles preferably contain 5% to 30% w/v of insulin to monomer content, more especially 15–25% w/v insulin.

The size of the biodegradable nanoparticles suitably is 50–900 nm, preferably 100–400 nm.

The polyalkylcyanoacrylate-complexed insulin-loaded nanoparticles in accordance with the invention and, optionally, free insulin-loaded polyalkylcyanoacrylate nanoparticles, if present, are suitably incorporated into oral dosage forms, such as capsules, tablets, powders including powders capable of effervescing upon addition of water, or suspensions. Additionally, an enteric coating can be applied to the polyalkylcyanoacrylate-complexed insulin-loaded nanoparticles and, optionally, free insulin-loaded polyalkylcyanoacrylate nanoparticles, if present, to protect the formulation while it passes though the stomach to further target release of insulin to the small intestine. Alternatively, the nanoparticles can be administered parenterally to release insulin to mimic physiological insulin needs.

Thus, for convenient and effective oral administration, pharmaceutically effective amounts of the nanoparticles of this invention can be tabletted with one or more excipient(s), encased in capsules such as gel capsules, formulated with ingredients which upon addition of water, provide an effervescent solution, and suspended in a liquid solution and the like. The nanoparticles can be suspended in a saline solution or the like for parenteral administration.

When the nanoparticles are tabletted, the tablets optionally comprise an enteric coating on the tablet to target release of insulin to the small intestine when administered orally.

It will be appreciated that the pharmaceutical formulations in accordance with the invention can be use inter alia to provide exogenous insulin to patients with type II diabetes or to treat non-insulin dependent diabetes. Suitably, a therapeutic amount of the formulation of this invention is administered to humans at an insulin dose, which varies from individual to individual, such that the blood glucose levels are adjusted to stay within normal ranges. The oral formulations preferably are designed as 4-times daily products while the parenteral formulations, which typically have >100 IU of bioavailable insulin per ml, can be administered once or twice daily up to once weekly.

IV. BRIEF DESCRIPTION OF THE DRAWINGS

Figure 2:
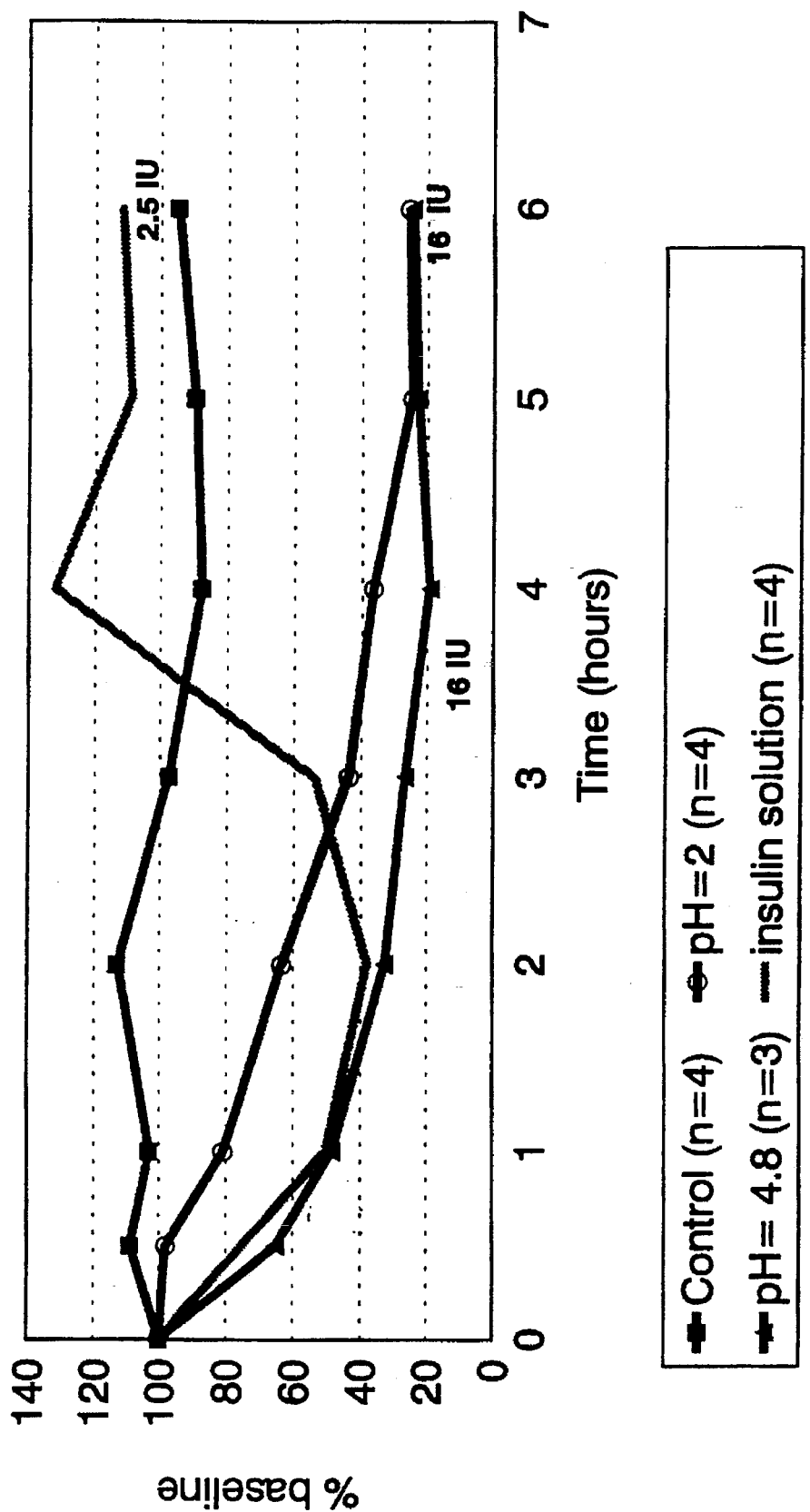
Figure 3:
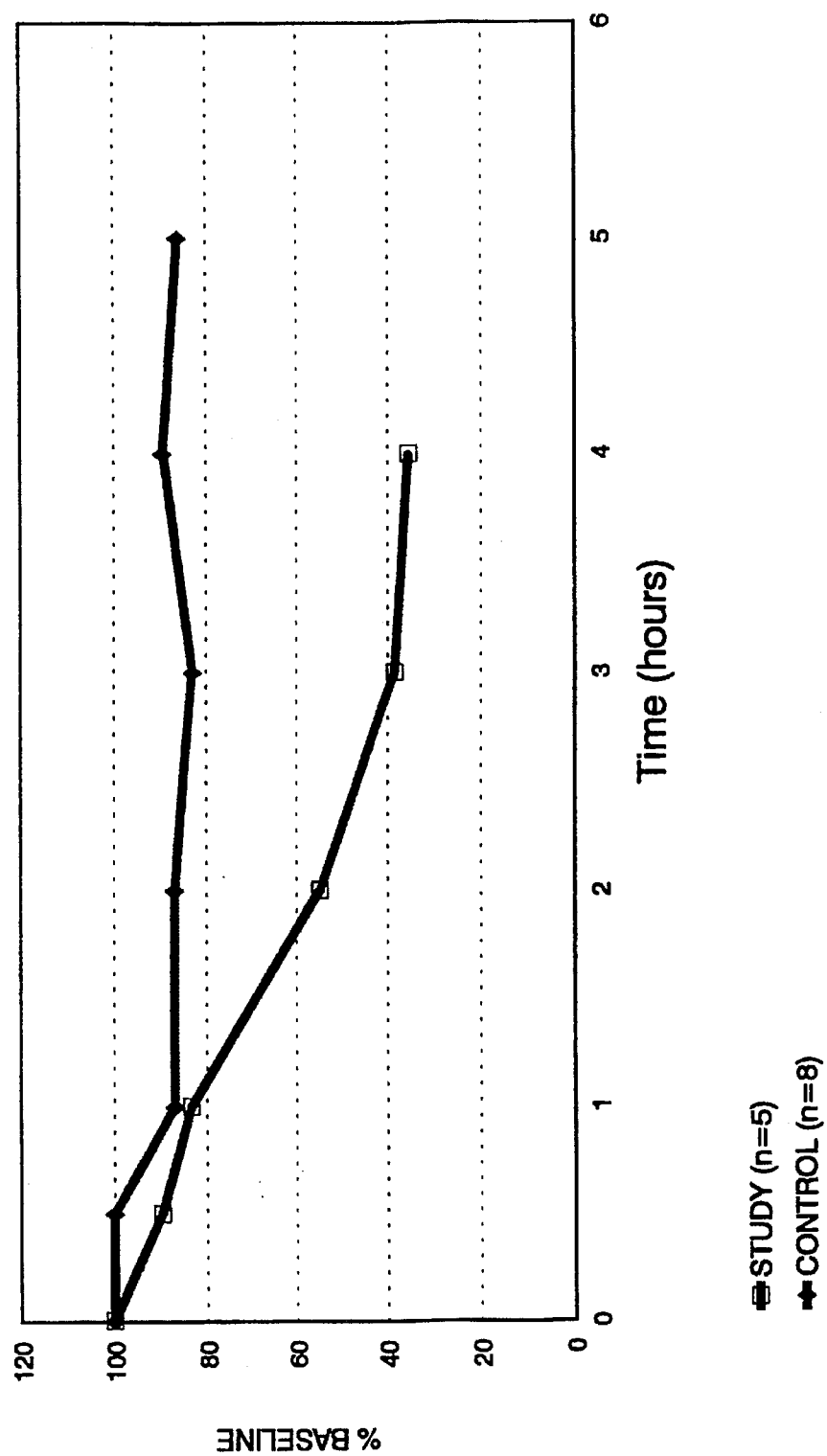

FIG. 1 shows the mechanistic pathway for the anionic polymerisation method of forming polyalkylcyanoacrylate nanoparticles;

FIG. 2 shows blood glucose levels over six hours expressed as a percentage of baseline values for four groups of male Wistar rats: Control (n=4; untreated rats); insulin solution (n=4; solution containing 2.5 IU insulin administered by IM injection to each rat at time 0); pH=2 (n=4; aqueous suspension of insulin-loaded polyalkylcyanoacrylate nanoparticles (16 IU) produced at pH=2 administered by IM injection to each rat at time 0); and pH=4.8 (n=3; aqueous suspension of insulin-loaded polyalkylcyanoacrylate nanoparticles (16 IU) produced at pH 4.8 administered by IM injection to each rat at time 0); and FIG. 3 shows blood glucose levels over 4 hours expressed as a percentage of baseline values for two groups of male Wistar rats: Control (n=8; untreated rats) and Study (n=5; aqueous suspension of insulin-loaded polyalkylcyanoacrylate nanoparticles (204 IU) produced at pH=2 administered orally to each rat at time 0).

V. DETAILED DESCRIPTION OF THE INVENTION

As used herein, the term "insulin" refers to insulin and analogues of insulin having similar physical properties.

As used herein, the term "polyalkylcyanoacrylate" refers to poly(2–12 C (straight or branched chain) alkyl 2-cyanoacrylates. Preferred polyalkylcyanoacrylates include polymers formed from 4–6 C alkylcyanoacrylates monomers such as n-butylcyanoacrylate, isobutylcyanoacrylate and isohexylcyanoacrylate or mixtures thereof.

As used herein, the term "biodegradable" as applied to polyalkylcyanoacrylate polymers means polymers which are degradable in vivo either enzymatically or non-enzymatically to produce biocompatible or non-toxic by-products which can be further metabolized or excreted via normal physiological pathways.

In the following Examples, n-butylcyanoacrylate was donated by Loctite Ltd. (Ireland). Isobutylcyanoacrylate, Dextran 10, 40 and 70 and insulin (bovine) were obtained from Sigma. Surface morphology of the nanoparticles produced was studied by scanning electron microscopy (SEM) (Leica Cambridge S360). Drug loading was monitored by the method of residuals using UV spectroscopy and by gradient HPLC analysis according to USP XXII. Male Wistar rats were used in the in vivo studies and blood glucose levels were monitored by an Ames™ Glucostix system.

Example 1: Effect of Choice of Monomer upon Nanoparticle Characteristics

Biodegradable polyalkylcyanoacrylate nanoparticles were produced from n-and isobutylcyanoacrylate using the anionic polymerisation method under standard conditions. For instance, for 20% starting drug loading, 100 mg of insulin was dissolved in 49.5 ml of a 0.01M HCl solution containing 0.5% Dextran 70 (as a stabiliser) prior to addition of the monomer. After adding the monomer, e.g., 0.5 ml isobutylcyanoacrylate, the solution was stirred for 4 hours, filtered or centrifuged and dried overnight. No difference in particle morphology between particles formed from n- or isobutylcyanoacrylate was observed under these conditions. The surface of particles produced were smooth, free of drug crystals and were 100 nm–400 nm in diameter. For a starting loading of 20% w/w, insulin loading values of 17.82% for n-butylcyanoacrylate and 17.97% for isobutylcyanoacrylate were obtained. Thus, the formation of insulin-loaded nanoparticles was not influenced by the choice of these monomers.

Example 2: Effect of Stabiliser Molecular Weight and Concentration upon Nanoparticle Characteristics Nanoparticles were produced using the method outlined in Example 1 to study the effect of varying the molecular weight of the stabiliser Dextran (using Dextran 10, Dextran 40 and Dextran 70; $M_w$=10,000, 40,000 and 70,000, respectively) at a concentration of 0.5% w/v on nanoparticle formation. Additionally, using Dextran 70, the concentration of the Dextran was also varied from 0.05 to 1% w/v. As shown in Table 1, no difference in nanoparticle size and morphology or in insulin entrapment efficiency was observed when either the molecular weight or concentration of the Dextran used was varied. This result for insulin-loaded polyalkylcyanoacrylate nanoparticles is contrary to that reported for empty polyalkylcyanoacrylate nanoparticles (Douglas, S. et al., *J. Colloid Interface Science*, 103:154–63 (1985).

TABLE 1

| Influence of Molecular Weight and Concentration of Dextran on Insulin Loading of Nanoparticles | | |
|---|---|---|
| Dextran Type | Dextran Concentration (% w/v) | Insulin Loading (% w/w) |
| Dextran 10 | 0.50 | 18.00 |
| Dextran 40 | 0.50 | 16.90 |
| Dextran 70 | 0.05 | 18.04 |
| Dextran 70 | 0.10 | 18.53 |

TABLE 1-continued

Influence of Molecular Weight and Concentration of Dextran on Insulin Loading of Nanoparticles

| Dextran Type | Dextran Concentration (% w/v) | Insulin Loading (% w/w) |
| --- | --- | --- |
| Dextran 70 | 0.25 | 18.25 |
| Dextran 70 | 0.50 | 19.07 |
| Dextran 70 | 1.00 | 18.18 |

Example 3: The Effect of Polymerisation Medium pH upon Nanoparticle Characteristics Insulin-loaded n-butylcyanoacrylate nanoparticles were produced using the method outlined in Example 1 to study the effect of varying the pH of the polymerisation medium from 1 to 4.8 on nanoparticle formation. As the pH of the polymerisation medium was increased above 3, defined, distinct particles were produced having smooth, drug-crystal free surfaces. However, below a pH of 3, formation of distinct nanoparticles appeared to be limited, showing only small quantities of well-formed nanoparticles. At this low pH, the formation of particles occurs quickly, resulting in the majority of nanoparticles not being well formed.

Additional experimentation shows that a white frothy precipitate results when insulin, at 10% and 20% w/v of monomer content, is first dissolved in a 0.1M HCl solution containing 0.5% w/v Dextran 70 to which 0.25 ml isobutylcyanoacrylate monomer is added. The precipitate can be collected by filtration and dried to give a fine white powder (100–400 nm). This reaction does not occur in the absence of insulin in the HCl solution or if the insulin is added after the cyanoacrylate monomer.

Without being bound by any theoretical explanation, it is suggested that these observations may be explained, with hindsight, by reference to the mechanism by which anionic polymerisation occurs and the physicochemical properties of insulin. As shown in FIG. 1, the hydroxyl ions present in the aqueous polymerisation medium initiate polymerisation. Because insulin is a peptide with an isoelectric point of 5.3, at a pH below 5.3 it is positively charged, while at a pH greater than 5.3, insulin is capable of being negatively charged. At low pH (pH <2), the insulin molecule has a net charge of +6 and can complex with the negatively charged cyanoacrylate short chains resulting in a termination of the polymerisation process. As the pH of the polymerisation medium is increased to 5, the net charge on insulin approximates zero and, therefore, complexation with the cyanoacrylate short chains is unlikely. At that pH, well formed insulin-loaded nanoparticles are produced.

HPLC analysis of insulin content of the nanoparticles produced at pH 2 yielded no insulin peaks at the expected insulin retention time. However, UV analysis (by the method of residuals) indicated >80% drug entrapment. HPLC analysis of nanoparticles produced at pH 4.8 showed the presence of insulin at the expected retention time of 19 minutes. These observations support the conclusion that, at low pH, insulin is complexed with the polymer and is not being eluted at the expected retention time for free insulin whereas at pH 4.8, free insulin is incorporated in the nanoparticles and is eluted at the expected retention time.

To support this conclusion, the formation of empty nanoparticles within the same pH range was investigated in order to establish if the presence of insulin inhibits nanoparticle formation at low pH. Nanoparticles were produced at pH 2, 3 and 4 under the same conditions as those employed for the insulin-loaded nanoparticles. In all cases, the nanoparticles produced were smooth, spherical and uniform in size. Thus, at low pH, the presence of insulin in the polymerisation medium interferes with nanoparticle formation.

Example 4: Intramuscular Administration of Insulin-loaded Nanoparticles to Rats The bioactivity and release properties of the insulin-loaded n-butylcyanoacrylate nanoparticles produced according to Example 3 were examined by intramuscular (IM) administration to male Wistar rats. Insulin-loaded nanoparticles produced at pH 2 (16 IU) and pH 4.8 (16 IU) were administered in aqueous suspension by IM injection to two groups of rats and blood glucose levels were monitored over a six hour period. Pure insulin solution (2.5 IU) was administered by IM injection to a third group of rats to provide a comparison between delivery via the nanoparticulate formulations and unencapsulated insulin. The blood glucose levels of untreated rats (controls) were also monitored over the same time period.

FIG. 2 shows the blood glucose levels for the pH 2, pH 4.8, control and untreated groups expressed as a percentage of baseline values. Blood glucose levels in the untreated group were within 87.6 to 108.9% of the baseline value in the study period. Administration of the nanoparticles resulted in a steady reduction in blood glucose levels to 20% of the baseline value, indicating that the insulin from the both types of nanoparticles (complexed at pH 2; free insulin at pH 4.8) is bioactive and is released in a controlled, sustained fashion. The blood glucose reduction was faster for nanoparticles produced at pH 4.8 than for those produced at pH 2, presumably due to the faster release of free insulin from the pH 4.8 formulation as opposed to the slower release of insulin complexed with polyalkylcyanoacrylate in the pH 2 formulation.

Example 5: Oral Administration of Insulin-loaded Nanoparticles to Rats

The bioactivity and release properties of the insulin-loaded n-butylcyanoacrylate nanoparticles produced according to Example 3 were examined by oral administration to male Wistar rats. Insulin-loaded nanoparticles produced at pH 2 were administered orally in an aqueous suspension to a group of rats and blood glucose levels were monitored over a four hour period. The dose administered per rat was 204 IU of insulin. The blood glucose levels of untreated rats were also monitored over the same time period.

FIG. 3 shows the blood glucose levels for these two groups expressed as a percentage of baseline values. Blood glucose levels in untreated rats were between 85 and 100% of the baseline value during the study period. In the treated rats, a reduction in blood glucose levels to 35% of the baseline value was observed over a four hour period, indicating an oral bioavailability of >7% for these insulin-loaded nanoparticles. These results indicate that the insulin from nanoparticles produced at pH 2 (complexed to the polyalkylcyanoacrylate) is bioactive and is released in a controlled, sustained fashion.

What is claimed is:

1. A controlled release pharmaceutical formulation, which comprises insulin entrapped in a biodegradable polyalkylcyanoacrylate polymer to form nanoparticles, wherein the insulin is complexed to the polyalkylcyanoacrylate.

2. A controlled release pharmaceutical formulation according to claim 1, wherein the polyalkylcyanoacrylate is formed from n-butylcyanoacrylate, isobutylcyanoacrylate or isohexylcyanoacrylate monomers or mixtures thereof.

3. A controlled release pharmaceutical formulation according to any preceding claim, wherein the insulin loading ranges from about 5% to 30% w/v of monomer content.

4. A controlled release pharmaceutical formulation according to any preceding claim, further comprising free insulin-loaded polyalkylcyanoacrylate nanoparticles to form a mixture of polyalkylcyanoacrylate-complexed insulin-loaded nanoparticles and free insulin-loaded polyalkylcyanoacrylate nanoparticles.

5. A controlled release pharmaceutical formulation according to any preceding claim, further comprising an enteric coating on the polyalkylcyanoacrylate-complexed insulin-loaded nanoparticles to target release of insulin to the small intestine when administered orally.

6. A controlled release pharmaceutical formulation according to claim 4 or 5, further comprising an enteric coating on the free insulin-loaded polyalkylcyanoacrylate nanoparticles to target release of insulin to the small intestine when administered orally.

7. A controlled release pharmaceutical formulation according to claim 1, wherein the formulation is formulated as capsules, tables, powders, powders capable of effervescing upon addition of water, or suspensions.

8. A controlled release pharmaceutical formulation according to claim 7, wherein the formulation is formulated as tablets and further comprising an enteric coating on the tablet to target release of insulin to the small intestine when administered orally.

9. A controlled release pharmaceutical formulation according to claim 1 and adapted for oral administration.

10. A controlled release pharmaceutical formulation according to and adapted for parenteral administration.

11. A method of satisfying physiological insulin needs in a subject, comprising administering to the subject a therapeutic amount of a controlled release pharmaceutical formulation comprising insulin entrapped in a biodegradable polyalkylcyanoacrylate polymer to form nanoparticles, wherein the insulin is complexed to the polyalkylcyanoacrylate.

12. A method according to claim 11, wherein the polyalkylcyanoacrylate is formed from n-butylcyanoacrylate, isobutylcyanoacrylate or isohexylcyanoacrylate monomers or mixtures thereof.

13. A method according to claim 11, wherein the insulin loading ranges from about 5% to 30% w/v of monomer content.

14. A method according to claim 11, wherein the formulation further comprises free insulin-loaded polyalkylcyanoacrylate nanoparticles to form a mixture of polyalkylcyanoacrylate-complexed insulin-loaded nanoparticles and free insulin-loaded polyalkylcyanoacrylate nanoparticles.

15. A method according to claim 11, wherein the formulation further comprises an enteric coating on the polyalkylcyanoacrylate-complexed insulin-loaded nanoparticles to target release of insulin to the small intestine when administered orally.

16. A method according to claim 14, wherein the formulation further comprises an enteric coating on the free insulin-loaded polyalkylcyanoacrylate nanoparticles to target release of insulin to the small intestine when administered orally.

17. A method according to claim 11, wherein the formulation is formulated as capsules, tables, powders, powders capable of effervescing upon addition of water, or suspensions.

18. A controlled release pharmaceutical formulation according to claim 17, wherein the formulation is formulated as tablets and further comprises an enteric coating on the tablet to target release of insulin to the small intestine when administered orally.

19. A method according to claim 11, wherein the administration is oral administration.

20. A method according to claim 11, wherein the administration is parenteral administration.

21. A method according to claim 14, wherein the formulation further comprises an enteric coating on the polyalkylcyanoacrylate-complexed insulin-loaded nanoparticles and further comprises an enteric coating on the free insulin-loaded polyalkylcyanoacrylate nanoparticles.

22. A controlled release pharmaceutical formulation comprising nanoparticles formed from insulin and polyalkylcyanoacrylate using the anionic polymerization method, wherein the pH of the polymerization medium is below a pH of 3.

* * * * *